United States Patent
Shaughnessy, Jr. et al.

(10) Patent No.: US 8,501,702 B2
(45) Date of Patent: Aug. 6, 2013

(54) OVEREXPRESSION OF WNT LIGANDS AND TREATMENT OF LYTIC BONE DISEASES

(75) Inventors: John D. Shaughnessy, Jr., Roland, AZ (US); Ya-wei Qiang, Little Rock, AR (US); Shmuel Yaccoby, Little Rock, AR (US)

(73) Assignee: Broad of Trustees of the University of Arkansas, Little Rock, AR (US)

( * ) Notice: Subject to any disclaimer, the term of this patent is extended or adjusted under 35 U.S.C. 154(b) by 696 days.

(21) Appl. No.: 11/999,301

(22) Filed: Dec. 4, 2007

(65) Prior Publication Data

US 2008/0193515 A1     Aug. 14, 2008

Related U.S. Application Data

(60) Provisional application No. 60/873,134, filed on Dec. 6, 2006.

(51) Int. Cl.
*A61K 48/00* (2006.01)
*A61K 39/395* (2006.01)

(52) U.S. Cl.
USPC ...... 514/44 R; 514/16.7; 514/19.3; 424/130.1

(58) Field of Classification Search
USPC .................... 514/44 R, 16.7, 19.3; 424/130.1
See application file for complete search history.

(56) References Cited

U.S. PATENT DOCUMENTS

| 2004/0265808 A1 * | 12/2004 | Garcia et al. ...................... 435/6 |
| 2006/0019895 A1 * | 1/2006 | Shaughnessy .................. 514/12 |
| 2006/0068494 A1 * | 3/2006 | Perreault ....................... 435/325 |

OTHER PUBLICATIONS

Yaccoby, S. et al. Antibody-Based Inhibition of DKK1 Suppresses Tumor-Induced Bone Resorption and Multiple Myeloma Growth in Vivo: *Blood*, Mar. 2007, vol. 109, No. 5, pp. 2106-2111.
Si, W. et al. CCN1/Cyr61 is Regulated by The Canonical Wnt Signal and Plays an Important Role in Wnt3A-Induced Osteoblast Differentiation of Mesenchymal Stem Cells: *Molecular and Cellular Biology*, Apr. 2006, vol. 26, No. 8, pp. 2955-2964.

* cited by examiner

*Primary Examiner* — Anne Marie S Wehbe
(74) *Attorney, Agent, or Firm* — Hamilton, Brook, Smith & Reynolds, P.C.

(57) ABSTRACT

The present invention is drawn to methods of repairing lytic bone lesions and tumor growth in an individual. In this regard, the present invention discloses use of a Wnt ligand either alone or in combination with anti-Wnt signaling antagonist therapy. The individuals who might benefit from such method may include but are not limited to the ones with multiple myeloma, osteoporosis, post-menopausal osteoporosis, fractures, metastatic breast cancer or metastatic prostate cancer.

24 Claims, 5 Drawing Sheets

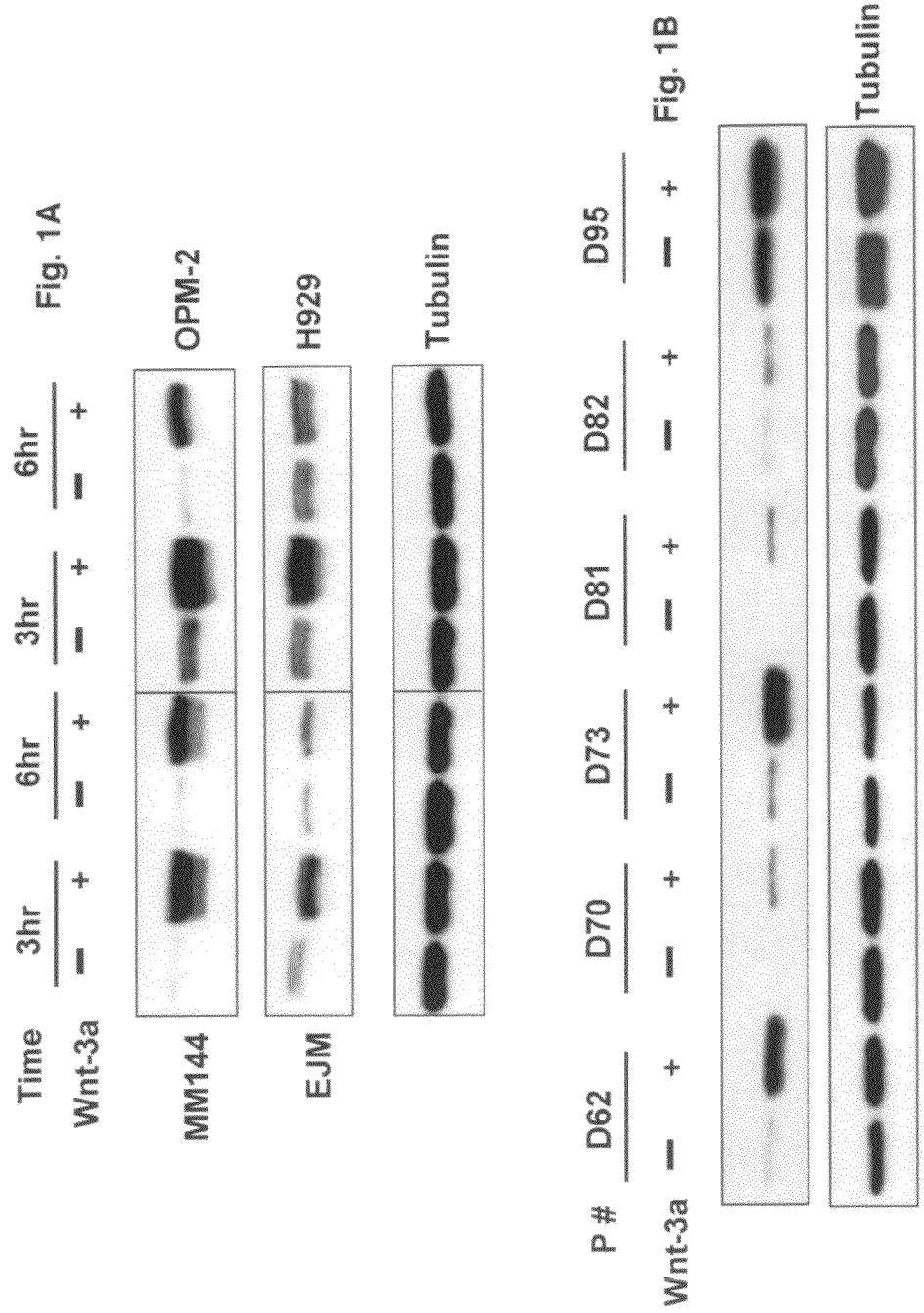

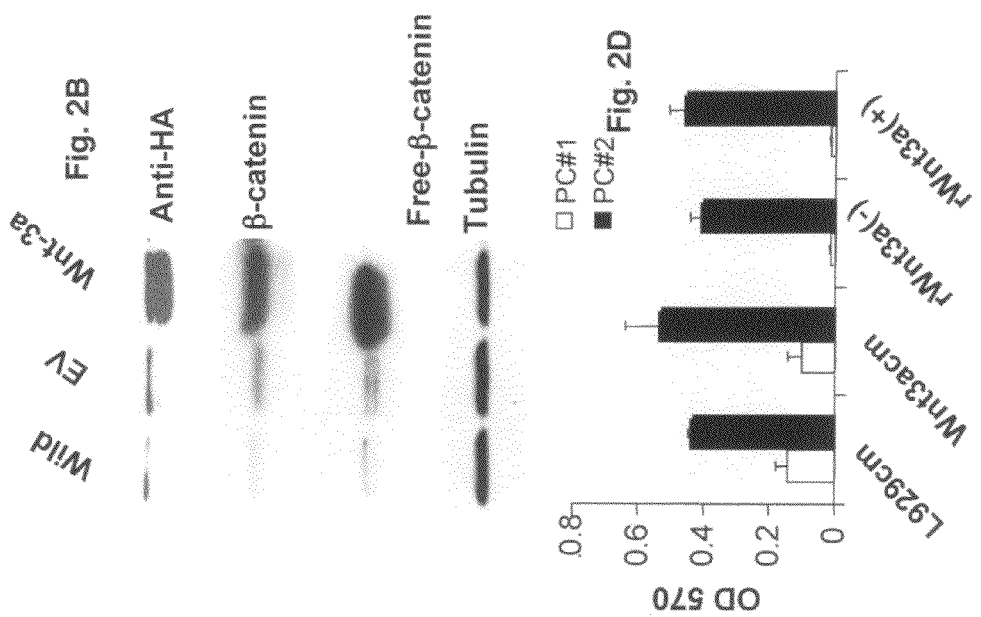
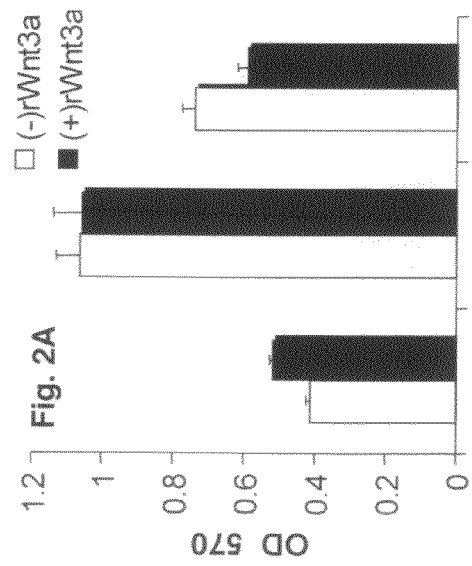
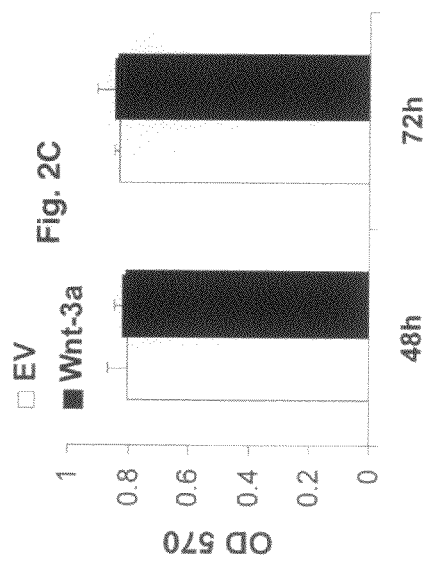

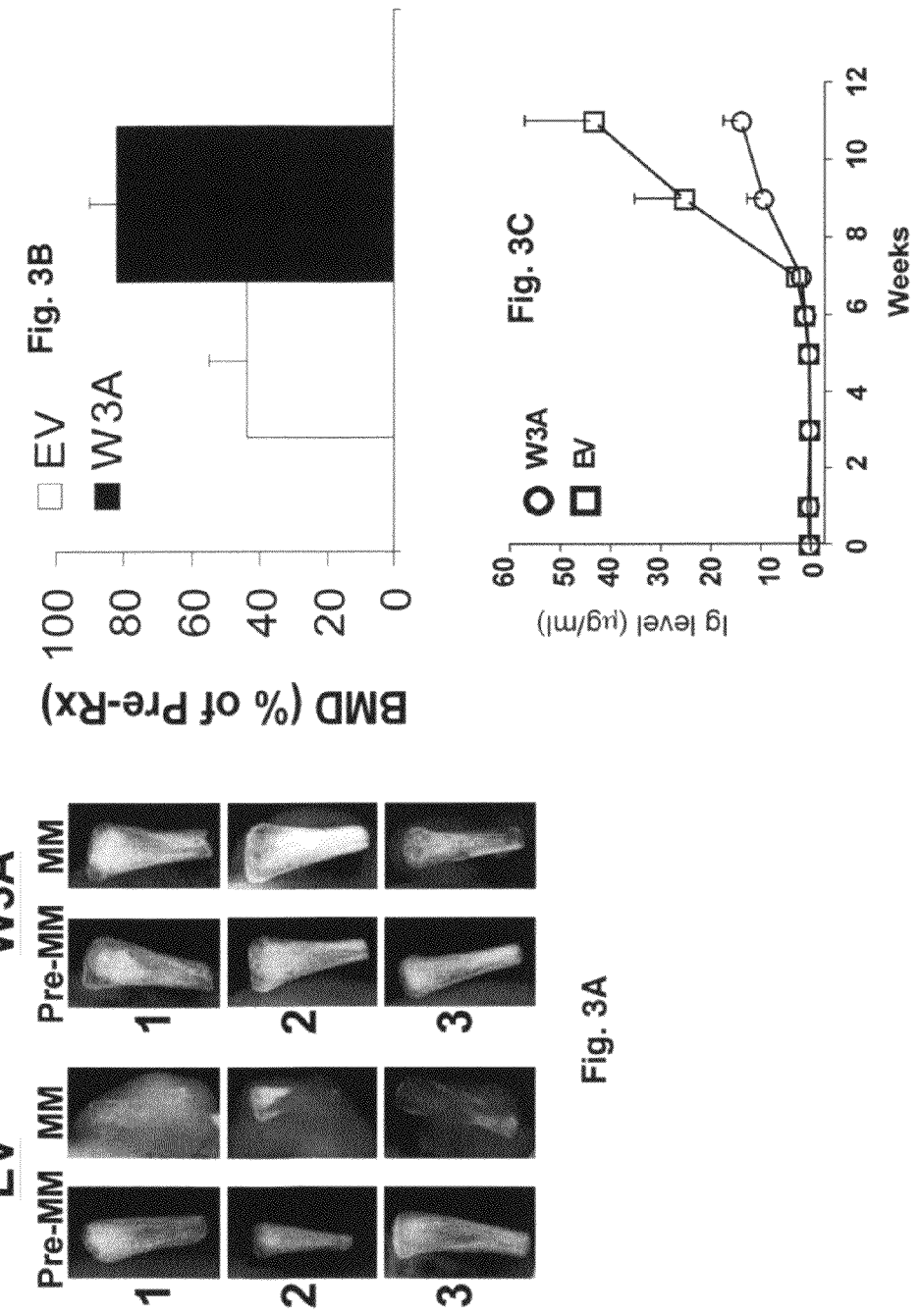

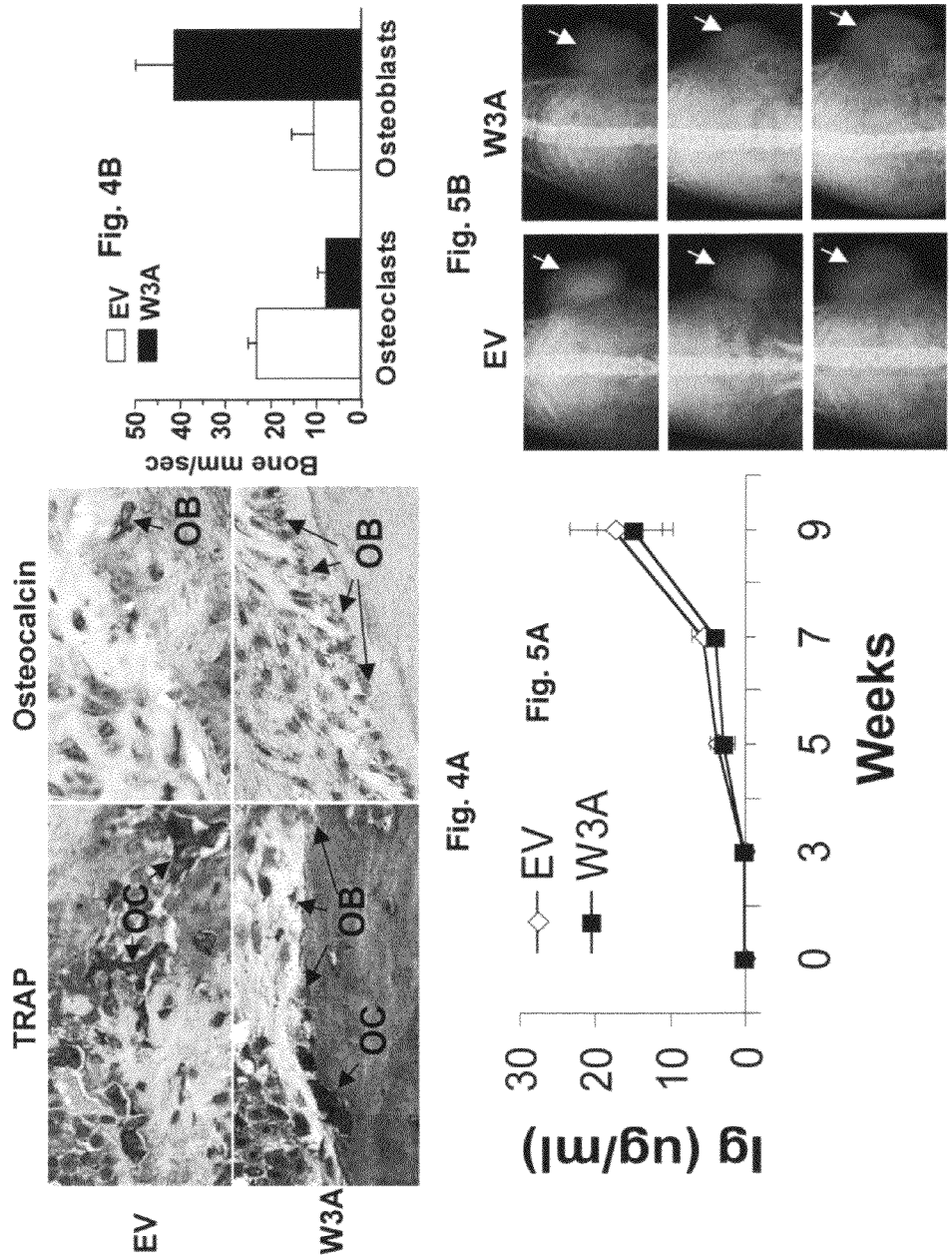

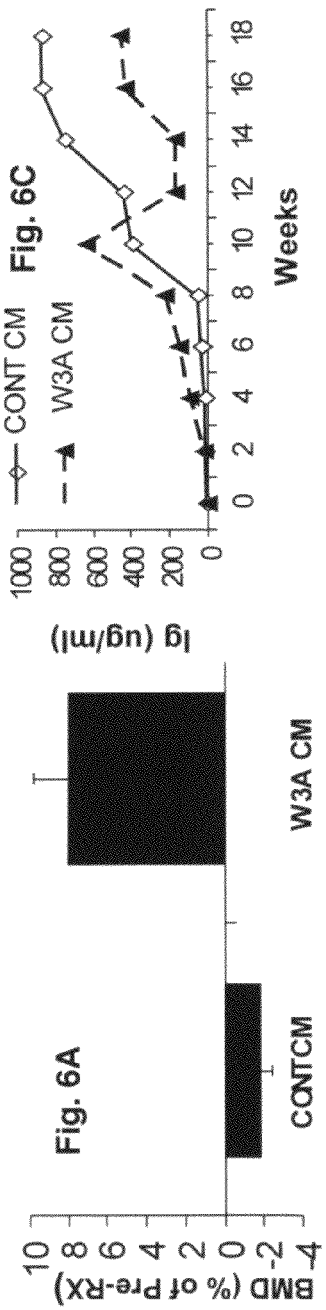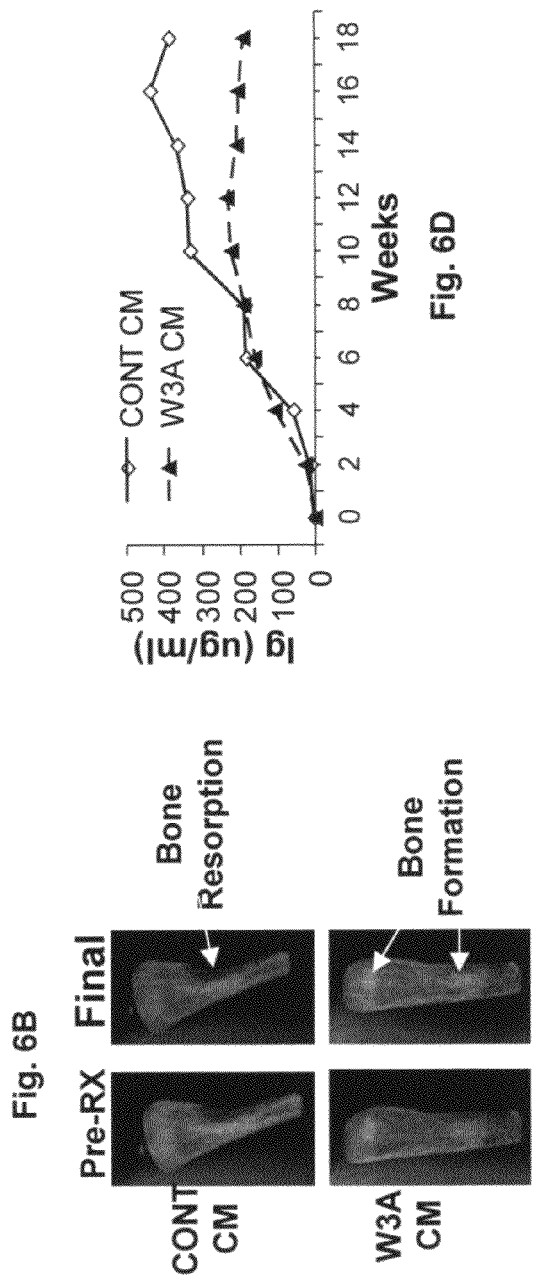

OVEREXPRESSION OF WNT LIGANDS AND TREATMENT OF LYTIC BONE DISEASES

CROSS REFERENCE TO RELATED APPLICATION

This non-provisional application claims benefit of provisional application U.S. Ser. No. 60/873,134 filed on Dec. 6, 2006, now abandoned.

FEDERAL FUNDING LEGEND

This invention was created, in part, using funds from the federal government under National Cancer Institute grants CA93897, CA55819 and CA97513. Consequently, the U.S. government has certain rights in this invention.

BACKGROUND OF THE INVENTION

1. Field of the Invention

The present invention relates generally to the study of Wnt signaling and lytic bone disease. More specifically, the present invention discloses methods for repairing lytic lesions and inhibiting tumor progression using Wnt ligands with or without anti-DKK1 therapy.

2. Description of the Related Art

Wnts comprise a highly conserved family of secreted glycoproteins consisting of 19 members. Wnt ligands bind to the Frizzled receptors alone or complexed with the low-density lipoprotein receptor-related proteins (LRP) 5/6. In vertebrates, Wnts can activate a 'canonical' b-catenin-dependent pathway or several b-catenin-independent 'noncanonical' pathways (Nusse, 2005; Veeman et al., 2003). The canonical Wnt-b-catenin pathway is normally repressed at several levels. An intracellular complex including GSK-3, axin, and the tumor suppressor gene product APC function to phosphorylate b-catenin, which in turn targets it for ubiquitin-mediated proteasomal degradation. Upon Wnt binding, b-catenin degradation is blocked leading to its accumulation and translocation to the nucleus, where it binds the TCF/LEF family of transcription repressors turning them into transcriptional activators (Nusse, 2005; van de Wetering et al., 2002).

Mounting evidence suggests that canonical Wnt signaling is central to normal skeletogenesis (Day et al., 2005; Kirstetter et al., 2006) and cancer related bone diseases (Johnson and Rajamannan, 2006; Stewart and Shaughnessy, 2006). The first direct evidence of role of Wnt signaling in bone formation came from seminal observations that inactivating mutations of the LRP5 gene caused osteoporosis-pseudoglioma syndrome (OPPG) (Gong et al., 2001). Subsequently, it was shown that a separate and distinct mutation in the same gene results in high bone density (Boyden et al., 2002; Little et al., 2002). Expression of Wnt10b in transgenic mice increased bone mass (Bennett et al., 2005) and overexpression of Wnt7B and beta-catenin in C3H10T1/2 osteoblastic precursor cells induced their differentiation into mature osteoblasts (Hu et al., 2005; Rawadi et al., 2003). Osteoclastogenesis is primarily regulated by receptor activator of the NF-kB ligand (RANKL) binding to RANK on the surface of osteoclast precursor cells. The ability of RANKL to bind RANK, and hence promote osteoclast development is tightly regulated by the RANKL decoy receptor, osteoprotegerin (OPG) (Lacey et al., 1998; Simonet et al., 1997). Remarkably, recent studies have shown that Wnt signaling in cells of the osteoblast lineage positively regulates the expression of OPG (Glass et al., 2005; Holmen et al., 2005) while negatively regulating RANKL (Spencer et al., 2006). Taken together these studies suggest that Wnt signaling is likely to be a central regulator of bone remodeling through its direct effects on osteoblastogenesis and indirect effects on osteoclastogenesis.

Multiple myeloma (MM) is a malignancy of plasma cells that uniquely accumulate in the bone marrow (BM), but not other organ systems, suggesting that the bone marrow provides unique growth and survival signals for MM cells. MM is characterized by osteolytic bone disease, which is caused by an uncoupling of bone remodeling as a result of increased osteoclast activity and decreased osteoblast activity (Bataille et al., 1991; Roodman, 2004; Taube et al., 1992). Over the last three decades numerous experimental and clinical studies have focused on the role of osteoclasts, and the identification of critical factors associated with increased osteoclast activity in MM (Sezer et al., 2003). However, it was recently observed that suppression of osteoblastogenesis by the soluble Wnt signaling inhibitor, Dickkopf-1 (DKK1), likely played critical role in MM-induced bone disease (Tian et al., 2003). DKK1 is the prototypical member of a family of secreted glycoproteins capable of inhibiting canonical Wnt signaling by binding to LRP5/6 causing it to be internalized and degraded (Binnerts et al., 2007). Wnt ligand interaction with its receptor can also be regulated by the secreted frizzled related proteins (sFRPs). As their name suggests, these factors are decoy receptors with frizzled domains capable of binding Wnts in solution (Finch et al., 1997). Interestingly, MM cells produce sFRP-2 (Oshima et al., 2005) and FRZB/sFRP-3 (de Vos et al., 2001; Zhan et al., 2002) and these factors may also contribute to the suppression of Wnt signaling in the bone marrow microenvironment (Stewart and Shaughnessy, 2006). It was recently shown that administration of a neutralizing antibody to DKK1 to myelomatous bones, presumably resulting in enhancement of Wnt signaling in the bone, prevented bone resorption and also tumor progression (Yaccoby et al., 2006). The importance of DKK1 secretion in diseases associated with bone destruction is reinforced by recent studies showing that a neutralizing antibody to DKK1 could inhibit the bone destructive process in rheumatoid arthritis (Sen, 2005).

As Wnt signaling activation has been linked to several forms of cancer, including blood malignancies (Polakis, 2000), the observation that neutralizing DKK1, and therefore enhancing Wnt signaling, has negative effects on MM tumor growth in bone, might be considered counterintuitive. However, it is now well recognized that an interaction between tumors and their associated stroma can dramatically influence tumor behavior (Karnoub et al., 2007). Therefore, it is possible that activation of the Wnt signaling pathway in the tumor-stroma milieu might override the effects of activating that signaling pathway in tumor cells when they are grown in a relatively static tissue culture environment.

Various clinical observations (Coleman et al., 2005) and experimental studies (Pearse et al., 2001; Vanderkerken et al., 2003; Yaccoby et al., 2004) have linked the level of MM bone disease with tumor progression. The notion that bone disease drives MM progression, at least in the initial phases of the disease process is also supported by studies demonstrating that osteoclasts alone can support long term survival and proliferation of primary MM cells (Yaccoby et al., 2004; Abe et al., 2004) and that osteoblastic cultures impede growth of MM cells from a large subset of patients (Yaccoby et al., 2006).

Despite this, the proliferative effects of Wnts in multiple myeloma are controversial. For instance, one study showed that Wnt could promote proliferation of multiple myeloma cells (Derksen et al., 2004) while another study was unable to show this effect (Qiang et al., 2003; Qiang et al., 2005). Thus, prior art lacks understanding of the role played by Wnt signaling in multiple myeloma and multiple myeloma-induced lytic bone disease. Additionally, prior art is deficient in means of repairing lytic lesions in patients with multiple myeloma and other cancers (breast cancer, prostate cancer) and inhibiting progression of the tumor. The present invention fulfills this longstanding need and desire in the art.

SUMMARY OF THE INVENTION

The present invention is directed to a method of repairing or treating lytic bone lesions in an individual. This method comprises expressing a Wnt ligand in the individual. The present invention is also directed to a method of preventing or reducing bone destruction in an individual. This method comprises administering pharmacologically effective amounts of Wnt ligand to the individual, where the Wnt ligand increases the ratio of osteoblast to osteoclast and bone mineral density, thereby preventing or reducing bone destruction in the individual.

The present invention is further directed to a method of inhibiting the progression of a tumor in the bone of an individual. This method comprises administering pharmacologically effective amounts of a Wnt ligand to the individual, where the Wnt ligand preventsor reduces bone destruction and inhibits growth of the tumor, thereby inhibiting progression of a tumor in the bone of the individual Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A-1B show that Wnt3a stabilizes β-catenin in MM cell lines and primary MM plasma cells. The myeloma cells were treated with Wnt3a-CM or Cont-CM for indicated time (FIG. 1A). Primary CD138 positive plasma cells from 6 MM patients confirmed by flow cytometry analysis were treated with Wnt3a-CM or Cont-CM for 3 hours (FIG. 1B). Proteins isolated from above treated cells were subjected to Western Blotting analysis. Total β-catenin was determined using an antibody that recognized the protein FIGS. 2A-2D show that WNT3a has no direct effect on growth of MM cell lines and primary MM cells. In FIG. 2A, cell froms indicated MM cell lines were cultured in serum-free medium in the presence of Cont-CM or Wnt3a-CM for indicated time. Cell proliferation was measured by MTT assay. In FIG. 2B, protein isolated from H929/W3a or H929/EV was subjected to Western Blotting analysis using anti-HA antibody to confirm Wnt3a expression (upper panel) or using anti-β-catenin antibody (second panel from top). The same fractions were also blotted with anti-tubulin antibody as a control for protein loading (bottom panel). The proteins isolated from H929/W3a of H929/EV was subjected to E-cadhesin-pull-down assay to measure the uncomplexed β-catenin (second panel from bottom). In FIG. 2C, H929/W3a and H929/EV cells were seeded in RPMI supplemented with 10% FBS for indicated time and proliferation was measured by MTT assay. In FIG. 2D, primary CD138-selected plasma cells from two MM patients (PC#1 and PC#2) were cultured in serum-free medium in the presence of Wnt3a-CM or Cont-CM or with rWnt3a protein for indicated time. Cell proliferation was measured by MTT assay.

FIGS. 3A-3C show that Wnt3A prevents bone loss and reduces tumor burden in myelomatous bones. SCID-hu mice were engrafted with H929/EV or H929/W3a cells. FIG. 3A shows X-ray radiographs of the implanted myelomatous bones taken from 3 representative mice in each group, before cell engraftment (Pre-multiple myeloma) and at the end (multiple myeloma). As opposed to EV-bearing bones that were severely resorbed and had tumors growing on the outer surface of the implanted bone, implanted bone mass from Wnt3A-bearing hosts was preserved. FIG. 3B shows changes in level of BMD of implanted bones engrafted with H929/EV or H929/W3a cells. FIG. 3C shows circulating human Ig level of SCID-hu mice engrafted with H929/EV or H929/W3a cells.

FIGS. 4A-4B show that Wnt3a increases osteoblastogenesis and reduces osteoclastogenesis in myelomatous bones. FIG. 4A shows decalcified histological bone sections of bones engrafted with H929/W3a or H929/EV cells stained for TRAP (red) and osteocalcin (brown). FIG. 4B shows numbers of osteocalcin-expressing osteoblasts and TRAP-expressing multinucleated osteoclasts in implanted bones engrafted with H929/EV and H929/W3a cells.

FIGS. 5A-5B show that Wnt3a has no effect on subcutaneous MM growth in SCID mice. SCID mice were subcutaneously injected with H929/W3a or H929/EV cells. FIG. 5A shows that circulating human Ig levels were similarly increased in hosts engrafted with EV and W3a cells. FIG. 5B shows X-ray radiographs demonstrating similar tumor size (white arrows) in hosts with EV and W3a cells.

FIGS. 6A-6D show that Wnt3a stimulates bone formation and attenuates MM growth in SCID-hu mice. SCID-hu engrafted with MM cells from 2 patients were daily injected with Cont-CM and Wnt3a-CM into the surrounding area of implanted bones. FIG. 6A shows changes in BMD of the implanted bones from pre-treatment level. FIG. 6B shows X-ray radiographs demonstrating changes in myelomatous bone mass of hosts treated with Cont-CM and Wnt3a-CM. FIGS. 6C and 6D show circulating human Ig level of SCID-hu mice engrafted with MM cells from 2 patients. Arrow indicates initiation of treatment. The treatment was initiated when MM was established and that Wnt3a-CM attenuated MM growth.

DETAILED DESCRIPTION OF THE INVENTION

Wnt signaling has emerged as a powerful signaling cascade regulating bone metabolism and secretion of Wnt signaling antagonist by MM cells is thought to contribute, in part, to the bone destructive process and perhaps MM disease progression. Although bisphosphonates have been shown to effectively slow the progression of the lytic process in MM (Berenson et al., 1996), osteonecrosis of the jaw is now recognized as a serious potential side-effect of their long term use (Bamias et al., 2005) and bone anabolic treatment strategies are still needed.

The present invention demonstrates that direct delivery of Wnt3a to myelomatous bones can inhibit bone destruction and tumor growth, confirms and extends previous studies suggesting that enhancing Wnt signaling in myelomatous bones, through neutralizing DKK1 activity, has similar effects. The lack of an effect of Wnt-3A secretion by H929/

W3A cells to suppress growth of these cells when engrafted subcutaneously, suggests that activation of Wnt signaling in the bone exerts its anti-tumor activity by promoting mesenchymal stem cells (MSC) differentiation into osteoblasts and subsequent suppression of osteoclastogenesis. These results are in line with previous studies demonstrating the negative impact of osteoclast inhibition (Coleman et al., 2005; Yata and Yaccoby, 2004; Bamias et al., 2005) and increased bone formation (Hall et al., 2005) on MM progression.

It was observed that canonical Wnts do not have growth-promoting effects on MM cells. The results described herein are reminiscent of the conclusions of a study by Hall and colleagues who showed that inactivating DKK1 in PC-3 prostate cancer cells caused them to revert from an osteolytic to an osteoblastic phenotype (Hall et al., 2005) that could be traced to the expression of canonical Wnts in these cells. Interestingly, like the observations in MM, there was no appreciable effect of loss of DKK1 expression (increased Wnt signaling) on PC-3 tumor growth. Indeed, the present invention reveals that like PC-3 cells, MM growth is unaffected by Wnts in-vitro and inhibited by a Wnt-induced osteoblastic response in the bone. This finding is even more remarkable given the fact that unlike primary disease, H929 cell growth is independent of stromal cell support and suggests that the osteoblastic response has a direct anti-myeloma effect, the basis of which remains obscure. These results are also consistent with recent studies showing that the anti-myeloma effects of the proteasome inhibitor bortezomib was linked to an osteoblastic response (Zangari et al., 2007) and that bortezomib inhibits DKK1 production in osteoblast precursors (Oyajobi et al., 2007) and does not induce DKK1 production in MM cells (Colla et al., 2007). The lack of a growth promoting effect of Wnt on MM cells, while having a bone anabolic and anti-tumor effects suggests that restoring Wnt signaling or enhancing it may have therapeutic benefit in this disease.

With the possibility that the beneficial effects of Wnt signaling in the bone marrow of MM is through its ability to drive the differentiation of mesenchymal stem cells (MSC) into osteoblasts, it is interesting to note that a recent study has shown that bone marrow-derived MSC promote the metastatic potential of the breast cancer line MDA-MB-231 (Karnoub et al., 2007). MDA-MB-231 cells produce high levels of DKK1, which may contribute to induction osteolytic bone metastases by these cells by suppression of MSC into osteoblasts. Thus, similar to a DKK1-mediated MM/MSC crosstalk that leads to high level secretion of IL-6 by MSC and growth promotion of IL-6-dependent MM cell lines (Gunn et al., 2006), the crosstalk between MDA-MB-231 cells and MSC, through DKK1, may be central to their metastatic phenotype. Hence, it will be interesting to see if DKK1 production by MDA-MB-231, and perhaps MM, influences the ability of MSC to induce a metastatic phenotype. It is intriguing to speculate that high levels of Wnt signaling inhibitors in MM bone marrow may also influence MSC in a way that promotes an intramedullary metastatic phenotype in patients with MM, a disease sometimes characterized by hundreds of MRI-defined metastatic intramedullary plasma cell foci with greater than eight of such foci being linked to a poor prognosis in this disease (Walker et al., 2007).

While Wnt signaling has been shown to be an activated response to Wnt3a stimulation, the direct effect of such signaling activation on MM cell growth is controversial (Qiang et al., 2003; Derksen et al., 2004). In the present invention, it was observed that Wnt3a or Wnt3a-CM had no effect on growth of MM cells in vitro, nor did overexpression of Wnt3a in MM cells confer a growth advantage in vitro and in when grown subcutaneously in SCID mice. These findings support the previous report that activation of canonical Wnt signaling by Wnt3a or by lithium chloride, which inhibits GSK3, had no effect on proliferation of MM cells nor conferred anti-apoptotic signals (Abe et al, 2004; Qiang et al., 2006). Furthermore, the present data provide evidence that Wnt3a does not synergize with IL6 and IGF-1, which serve as two major proliferative and survival factors in MM cells (Qiang et al., 2002; Qiang et al., 2004). Previous studies also revealed that DKK1, which is thought to be a tumor suppressor and mediator of apoptosis (Grotewold and Ruther, 2002; Mikheev et al., 2004), had no effect on MM cell apoptosis, and its forced overexpression could not inhibit cell growth or sensitize MM cells to apoptosis following treatment with thalidomide or lenalidomide (Qiang et al., 2003; Colla et al., 2007).

It is understood that beta-catenin activity is tightly controlled by ubiquitin mediated proteasomal degradation following phosphorylation by GSK3β(Cook et al., 1996). Inhibition of proteasome activity has been shown to promote osteoblast survival and differentiation by prevention of Runx2 degradation in osteoblasts precursors (Bellido et al., 2003). Bortezomib has been shown to stimulate osteoblast activity (Zangari et al., 2007; Zangari et al., 2005) and Runx2 expression in the BM of MM patients (Giuliani et al., 2007). Intriguingly, although bortezomib also stimulated Wnt signaling in MM cells (Qiang & Shaughnessy, unpublished data, 2007) this compound has been shown to inhibit MM cell growth in vitro at low nanomolar levels (Mitsiades et al., 2003) suggesting that stabilization of beta-catenin in MM cells by bortezomib has no impact on survival of MM cells. These studies indicate that activation or suppression of Wnt signaling has no direct effect on MM cell growth.

Other studies, however, showed that Wnt ligands could promote MM cell growth in vitro (Derksen et al., 2004), and that PKF115-584, a compound that disrupts beta-catenin TCF-regulated transcriptional complex formation inhibited growth of MM cells in vitro and in a xenograft model in which tumor cells grow in intra- and extra-osseous and extramedullary sites (Sukhdeo et al., 2007). The conflicting findings in those studies require further clarification. For instance, PKF115-584 was shown to exert serious adverse side effects in mice including severe bone marrow hypoplasia while in vitro abolished the protective effect of IL-6 on MM cells. Since IL-6 serves as a growth factor for MM via activation of MAPK and PI-3 kinase pathways, which are not downstream targets of Wnt signaling in myeloma (Qiang et al., 2005) and in vivo MM typically progresses through cultivation of the BM microenvironment, this compound may affect MM growth indirectly through inhibition of other signaling pathways and induction of nonspecific bone marrow hyperplasia. Taken together, it is believed that since growth of MM cells from the majority of patients is restricted to bone and requires an altered bone marrow microenvironment the consequences of activation of Wnt signaling on MM should be experimentally tested in conditions that typically mimic clinical MM. Recently, Edwards and colegues (Edwards et al., 2007) demonstrated that the Wnt signaling activator, lithium chloride, had no effect on growth of 5TGM1 MM cells in vitro but inhibited growth of these cells in bone, presumably through indirect effects on the bone marrow microenvironment. Activation of Wnt signaling in early B cell progenitors resulted in inhibition of their survival and growth in co-culture with adult bone marrow stromal cells (Dosen et al., 2006) while induced growth of pro-B cells from fetal liver (Reya et al., 2000). These studies further indicate the important role of the microenvironment in regulation of the behavior of both normal and tumor cells by Wnt signaling.

The data herein indicate that overexpression of Wnt3a has marked inhibitory effect on MM-induced osteolytic bone lesions although activation of Wnt signaling has no effect on growth of MM cells in vitro and that increasing Wnt signaling suppresses tumor growth in bone marrow microenvironment. The present invention contemplates the mechanism by which Wnt signaling suppresses in vivo tumor growth.

Although the present invention demonstrated repairing the lytic lesions associated with multiple myeloma, it is contemplated that the method can be used to repair lytic lesions associated with other malignancies, including but not limited to breast cancer and prostate cancer. Additionally, it is also contemplated that the method can be used to promote more rapid effective healing of bone fractures in the elderly. Furthermore, although the present invention demonstrated repairing the lytic lesions with Wnt-3a protein, it is contemplated that other canonical Wnt ligands such as Wnt-1, Wnt-2 or Wnt-10b will be equally effective. The Wnt-3a protein may be directly administered at the site of a lytic lesion to promote osteoblast differentiation and spontaneous healing. However, there may be a reluctance to use Wnt-3a systemically because of its putative tumor promoting effects. This possibility may be eliminated by local use, ex-vivo exposure of osteoblasts precursors and/or pulsing the compound for short periods of time to avoid chronic exposure. Thus, pulsing Wnt-3a for short periods of time in-vivo might eliminate the unwanted pro-growth effects this molecule may have on cell types sensitive to Wnt signaling perturbation in cancers. Alternatively, osteoblast precursors pretreated with Wnt-3a for several hours ex-vivo and injected into the lytic site may also enable eliminating the unwanted pro-growth effects of this molecule. The Wnt ligands discussed herein may be administered as a gene encoding the Wnt ligand, a recombinant Wnt ligand protein or a Wnt ligand peptide.

Furthermore, the Wnt-3a treatment may be combined with anti-Wnt signaling antagonist therapy including but not limited to anti-DKK1 therapy. The anti-DKK1 therapy may be combined with Wnt-3a pulses for short periods of time either systemically or at the sites of local bone loss. This combination therapy may have profound bone anabolic effects in patients with myeloma and breast cancer bone metastasis. Additionally, the combination therapy may be used to promote more rapid effective healing of bone fractures in the elderly.

In one embodiment of the present invention, there is provided a method of repairing or treating lytic bone lesions in an individual comprising: expressing a Wnt ligand in the individual. This method may further comprise blocking activity of a Wnt signaling antagonist. Further, the activity of the Wnt signaling antagonist may be blocked prior to, concurrent with or subsequent to the expression of the Wnt ligand. Generally, the expression of the Wnt ligand either alone or in combination with the blocked activity of the Wnt signaling antagonist may induce bone anabolic effects in the individual and may inhibit tumor growth in the bone. Specifically, the anabolic effects may comprise inhibition of osteolysis and increasing bone mineral density. Examples of the WNT signaling antagonist may include but is not limited to the human homologue of Dickkopf-1 (DKK1), SFRP-3/FRZB or SFRP-2. Additionally, the activity of the Wnt signaling antagonist may be blocked by administering anti-DKK1 antibodies, DKK1 anti-sense oligonucleotides, anti-SFRP-3/FRZb antibodies, anti-SFRP-2 antibodies, SFRP-3/FRZB anti-sense oligonucleotides, SFRP-2 anti-sense oligonucleotides or small molecule inhibitors to the individual. Representative examples of the Wnt ligand may include but is not limited to Wnt-3a, Wnt-1, Wnt-2 or Wnt-10b.

The Wnt ligand may be expressed by over-expressing a gene encoding the Wnt ligand or administering a recombinant Wnt ligand protein or Wnt ligand peptide. The Wnt ligand may be expressed by administering pharmacologically effective amounts of the gene encoding the Wnt ligand, the recombinant Wnt ligand protein or the Wnt ligand peptide directly into the lytic site or by local and/or systemic pulsing for short period of time. Alternatively, the Wnt ligand may be expressed by pretreating osteoblast precursor cells with the gene encoding the Wnt ligand, the recombinant Wnt ligand protein or the Wnt ligand peptide for several hours ex-vivo and then injecting the treated precursor cells into the lytic site. Further, the gene may be delivered by a viral vector or a non-viral gene delivery system. Since use of a viral vector or a non-viral gene delivery system is routine in the art, one of skill in the art may any of the vectors or system that are being routinely used. Thus, a representative example of the viral vector may include but is not limited to an adenoviral vector or a lentiviral vector and those of the non-viral gene delivery system may include but is not limited to a liposome or a high pressure gene delivery system. Furthermore, the lytic bone lesion in the individual may due to a disease that includes but is not limited to multiple myeloma, osteoporosis, post-menopausal osteoporosis, fractures or malignancy-related bone loss. The maligancy related bone loss may be caused by breast cancer metastasis to the bone or prostate cancer metastasis to the bone.

In another embodiment of the present invention, there is provided a method of preventing bone destruction in an individual, comprising: administering pharmacologically effective amounts of Wnt ligand to the individual, where the Wnt ligand increases ratio of osteoblast to osteoclast and bone mineral density, thereby preventing bone destruction in the individual. This method may further comprise controlling tumor growth in the bone of the individual.

Additionally, the Wnt ligand may be administered either alone or in combination with pharmacologically effective amounts of a compound that blocks activity of a Wnt signaling antagonist. Furthermore, the activity of the Wnt signaling antagonist may be blocked prior to, concurrent with or subsequent to the expression of the Wnt ligand. All other aspects regarding the examples of the Wnt signaling antagonist, the compound blocking the activity of the Wnt signaling antagonist, examples of the Wnt ligand, the different ways and the manner in which the Wnt ligand is administered, examples of viral vector or a non-viral gene delivery system and the individual who may benefit from this method is the same as discussed supra.

In yet another embodiment of the present invention, there is provided a method of inhibiting progression of a tumor in the bone of an individual, comprising: administering pharmacologically effective amounts of Wnt ligand to the individual, where the Wnt ligand prevents bone destruction and inhibits growth of the tumor, thereby inhibiting progression of the tumor in the bone of the individual. Additionally, the Wnt ligand may be administered either alone or in combination with pharmacologically effective amounts of a compound that blocks activity of a Wnt signaling antagonist. Furthermore, the activity of the Wnt signaling antagonist may be blocked prior to, concurrent with or subsequent to the expression of the Wnt ligand. All other aspects regarding the examples of the Wnt signaling antagonist, the compound blocking the activity of the Wnt signaling antagonist, examples of the Wnt ligand, the different ways and the manner in which the Wnt ligand is administered, examples of viral vector or a non-viral gene delivery system and the individual who may benefit from this method is the same as discussed supra.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As discussed herein, the Wnt ligand described herein may be brought into contact with a cell culture system comprising osteoblast precursors. In vitro or ex vivo may be achieved by exposing the above-mentioned cell to the composition in a suitable medium. In vivo may be achieved by any known methods in the art.

The Wnt ligand may be administered prior to or concurrent with or subsequent to the compound that blocks the activity of Wnt signaling antagonists discussed herein. The effect of co-administration with the composition is to induce profound bone anabolic effects. The Wnt ligand either alone or in combination with the compound that blocks the activity of Wnt signaling antagonists may be administered either systemically or locally, by any method standard in the art. Dosage formulations of the compositions described herein may comprise conventional non-toxic, physiologically or pharmaceutically acceptable carriers or vehicles suitable for the method of administration and are well known to an individual having ordinary skill in this art.

The Wnt ligand described herein and the compound that blocks the activity of Wnt signaling antagonists may be administered independently one or more times to achieve, maintain or improve upon a therapeutic effect. It is well within the skill of an artisan to determine dosage or whether a suitable dosage of either or both of the composition and anti-cancer agent comprises a single administered dose or multiple administered doses. An appropriate dosage depends on the subject's health, the repair of the lytic bone lesion and prevention of tumor progression, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Myeloma Cells and Cell Lines

Multiple myeloma cells were obtained from heparinized BM aspirates from patients with active myeloma during scheduled clinic visits. Signed Institutional Review Board-approved informed consent forms are kept on record. CD138-expressing multiple myeloma cells were isolated as previously described (Zhan et al., 2002; Zhan et al., 2006).

The human MM cell lines, EJM, H929, INA6, MM144, OPM-2, SKMM-1 and U226 were cultured in RPMI1640 (Invitrogen, Carlsbad, Calif.) containing 10% heat-inactivated FBS, and 4 mM L-glutamine as described previously (Qiang et al., 2004; Qiang et al., 2002). Mouse pluripotent mesenchymal precursor cell line C2C12 was purchased from America Type Culture Collection (Manassas, Va.) and Saos-2 were cultured in Dulbecco's Modified Eagle Medium (DMEM) (Invitrogen, Carlsbad, Calif.) containing 10% heat-inactivated FBS, penicillin (100 U/ml), streptomycin (100 mg/ml) and 4 mM L-glutamine. Cells were maintained at 37° C. and humidified with 95% air and 5% $CO_2$ for cell culture.

Example 2

Preparation of Conditioned Medium

Wnt3a conditioned medium (Wnt3a-CM) or control (Cont-CM) was prepared as previously described (Qiang et al., 2003). Briefly, Wnt3a-producing L cells (stably transfected with Wnt3a cDNA provided by Dr Shinji Takata) or control L cells were cultured to become confluent in DMEM medium supplemented with 10% FCS after which the medium was replaced with serum-free DMEM. The culture supernatant was collected after 72 hours and designated Wnt3a-CM and con-CM, respectively. The concentration of Wnt3a in CM was evaluated by the ability to stabilize β-catenin using recombinant Wnt3a (R&D Systems, Minneapolis, Minn.). The concentration in 100% CM equates to the 150 to 200 ng/ml of recombinant Wnt3a to stabilization of b-catenin.

Example 3

Constructs and Transfectants

The Wnt3a-stable-expressing MM cell line was generated as previously described (Qiang et al., 2005). Briefly, H929 cells were transfected with plasmids encoding Wnt-3a cDNA or empty vector as using Lipofectamine (Invitrogen-Life Technologies, Inc.) according to manufacturer's instructions. Clonal cell lines were generated by limited dilution in growth media containing 1 mg/ml G418. Positive clones were detected by anti-HA antibody.

Example 4

Treatment of MM cells and Proliferation Assay

Growth of the MM cells was determined by cell viability and a non-radioactive cell proliferation assay system (MTT assay) (Qiang et al., 2000).-Briefly, H929, INA6 and OPM-2 cells and primary MM plasma cells ($5 \times 10^4$/ml) were cultured either in serum free medium with Wnt3a-CM, Control-CM or recombinant Wnt3a protein (100 ng/ml), IL-6 (10 ng/ml) or IGF-1 (100 ng/ml) (PeproTech, Rocky Hill, N.J.) in 96 well plates. At the indicated time points, 10 mL of 5 mg/mL MTT [3-(4,5-dimethylthiazol-2-yl)-2,5-diphenyl tetrazolliumbromide] was added to each well and incubated for 4 hours at 37° C., followed by incubation in 100 mL of 10% sodium dodecylsulfate (SDS) in 0.01N HCl at 37° C. overnight. The optical density of the plates was read on a Spectra MAX 340 Microplate Spectrophotometer (Molecular Deices, Calif.) at 570 nm. Recombinant mouse Wnt3a was purchased from R&D Systems. Human recombinant IGF-1 and IL6 were purchased from PeproTech (Rocky Hill, N.J.).

Example 5

Western Blotting

Cells were incubated in Wnt3a-CM or Control-CM for indicated times and solubilized in lysis buffer as described (Qiang et al., 2002). After incubation for 30 minutes at 4° C., cell debris and nuclei were removed by centrifugation at 15,000 rpm for 10 minutes at 4° C. Protein concentration was determined by BCA protein assay (Pierce, Rockford, Ill.). Proteins in lysate were separated with 8% sodium dodecyl sulfate (SDS)-polyacrylamide gels followed by electrophoretic transfer to Immobilon polyvinylidene difluoride membranes (Millipore, Bedford, Mass.). Membranes were blocked with 5% non-fat dried milk in Tris-buffered saline-Tween20 and incubated for 1 or 2 hours with a specified monoclonal antibody. Detection was performed by a standard procedure with the use of 0.2 g/mL of a panel of secondary horseradish peroxidase-conjugated antibodies and chemiluminescence (ECL, Amersham, Buckinghamshire). Anti-b-catenin antibody and horseradish peroxidase-conjugated anti-mouse antibodies were purchased from Transduction Laboratories (Lexington, Ky.).

Example 6

GST-E-Cadherin Binding Assay

The GST-E-cadherin binding assay was performed as described (Bafico et al., 1998). Briefly, the β-catenin binding site of E-cadherin as a GST-fusion protein was purified using GST beads. GST-E-cadherin was used to precipitate uncomplexed b-catenin present in 500 mg of cell lysate. Precipitated β-catenin was detected by Immunoblotting using a β-catenin monoclonal antibody Transduction Laboratories (Lexington, Ky.).

Example 7

Myelomatous SCID-hu Mice

SCID-hu mice were constructed as previously described (Yaccoby et al., 1998). H929/W3A and H929/EV H929 cells ($0.5 \times 10^6$ cells/mouse) were each injected directly into the implanted bone (n=6). Mice were weekly bled from tail vein and changes in levels of circulating human Ig (hIg) of the M-protein isotype were determined by ELISA as described (Yaccoby et al., 1998; Yaccoby et al., 1999) and used as an indicator of multiple myeloma growth. Radiographs were taken with an AXR Minishot-100 beryllium source instrument (Associated X-Ray Imaging Corp., Haverhill, Mass.). Changes in BMD of the implanted bone were determined using a PIXImus DEXA (GE Medical Systems LUNAR, Madison, Wis.) (Yaccoby et al., 2006). Experiment was ended after 11 weeks, at which time large tumor was apparent on outer surface of the implanted bone in control mice injected with H929/EV cells. For testing subcutaneous growth, H929/W3a and H929/EV cells ($5 \times 10^6$ cells/mouse) were each injected subcutaneously in SCID mice (n=5) and the experiment was ended 9 weeks from cell injection.

Example 8

Immunohistochemistry and Histochemistry

Human bones were decalcified with 10% (wt/vol) ethylenediaminetetraacetic acid (EDTA), pH 7.0. The bones were embedded in paraffin for sectioning. Sections (5-µm) were deparafinized in xylene, rehydrated with ethanol, rinsed in PBS and underwent antigen retrieval using microwave. After peroxidase quenching with 3% hydrogen peroxide for 10 min sections reacted with 5 µg/ml osteocalcin antibody (QED Bioscience Inc, San Diego, Calif.) and the assay was completed with the use of Dako's immunoperoxidase kit (Carpinteria, Calif.). Sections were lightly counterstained with hematoxylin (Yaccoby et al., 2004; Yata and Yaccoby, 2004). According to the Tartrate-resistant acid phosphatase (TRAP) staining of deparaffinized bone sections was performed with an acid phosphatase kit (Sigma, St. Louis, Mo.). Osteocalcin-expressing osteoblasts and TRAP-positive multinucleated osteoclasts in four nonoverlapping, millimeter-square areas were counted.

Example 9

Statistical Analysis

All values are expressed as mean±SEM. Student's t-test was used to test the effect of treatment on bone mineral density, myeloma burden, osteoblast and osteoclast numbers and in vitro proliferation. Significant p values were less than 0.05 by two-tailed test.

Example 10

Wnt3a Activates Wnt Signaling in MM Cells

The present invention examined the effect of Wnt3a on the stabilization of β-catenin in MM cell lines and primary MM plasma cells from 6 patients. Baseline levels of b-catenin varied between different MM cell lines and primary samples (FIG. 1). Wnt3a-CM (50% v/v) increased β-catenin protein level in a time-dependent manner in EJM, H929, MM144 and OPM-2 cells (FIG. 1A). Similar results were found in SKMM-1, U266, INA6 and ANBL6 MM cell lines (data not shown). b-catenin protein levels were highest at 3 hrs post Wnt3a treatment and decreased steadily over the subsequent 6 hours. Similar results were also seen in all six primary MM samples regardless of baseline level of b-catenin (FIG. 1B). These results indicated that Wnt3a consistently activates canonical Wnt signaling in MM cells.

Example 11

Activation of Wnt Signaling Has No Effect on MM Cell Growth In Vitro

Because of conflicting data in the literature on canonical Wnt effects on MM growth (Qiang et al., 2003; Derksen et al., 2004), the consequences of Wnt signaling activation on MM cell growth in vitro were examined. Exposure of H929, OPM-2 and the IL-6 dependent cell line INA6 to recombinant Wnt3a (rWnt3a) did not increase proliferation of the cells (FIG. 2A). Moreover, Wnt3a had no additive or synergistic effects on MM cell growth when combined with IGF-1 and IL-6 (data not shown).

To determine whether MM growth response to Wnt signaling is dependent on the maintenance of high Wnt3a concentration in cells, the MM cell line H929 were stably transduced with an expression construct containing Wnt3a cDNA (henceforth referred to as H929/W3a) or empty vector (henceforth referred to as H929/EV). As there are no commercial antibodies that recognize Wnt proteins, the Wnt3a gene was cloned as a HA (hemaglutanin) fusion protein. Western blot analysis with an anti-HA antibody showed clear recognition of an HA positive band of the expected size only in H929/W3a cells and not control H929/EV cells (FIG. 2B).

To determine whether H929/W3a cells produced a functional Wnt3a protein, the E-cadherin pull-down assay was utilized to detect uncomplexed β-catenin (Bafico et al., 1998). Western blot analysis was then performed to detect total level of β-catenin. Although H929/W3A, but not H929/EV cells, contained high levels of both forms of β-catenin (FIG. 2B), there was no difference in their growth rate in vitro in the presence of serum (FIG. 2C) or under serum-starved conditions (data not shown). The present invention also examined whether Wnt3a acts as a growth factor in primary MM cells by using both Wnt3a-CM and rWnt3a. Similar to that observed in MM cell lines, neither Wnt3a-CM nor rWnt3a promoted proliferation of primary plasma cells isolated from two MM patients (FIG. 2D), while the IGF-1 and IL-6 did (data not shown). Taken together, these results suggested that Wnt3a is not a growth factor necessary for MM cells to proliferate nor does it have anti-apoptotic, nor has synergized effect with other main growth factors like IL6 and IGF-1 in vitro.

Example 12

Overexpression of Wnt3a in MM Cells Inhibits Bone Disease and Tumor Growth in SCID-Hu Mice To determine the effect of canonical Wnt on MM growth and bone manifestation characteristics in vivo, the H929/W3a and H929/EV were transplanted into implanted human bone in SCID-hu mice. Growth of these cells was restricted to the implanted bone site. X-ray radiographs revealed that, as expected, bones injected with H929/EV control cells were severely resorbed and tumors spread on the outer surface of the implanted bone (FIG. 3A). In contrast the bones injected with H929/W3a cells were preserved even in cases where small tumor was apparent on the bone surface (FIG. 3A). Whereas BMD of bones injected with H929/EV cells was reduced by 56±11% from pre-treatment levels, BMD in bones engrafted with H929/W3A cells was reduced buy 18±9% from pretreatment level (p<0.02, H929/EV vs. H929/W3A groups, FIG. 3B).

Changes in level of tumor burden were determined by periodical hIg measurement (Yaccoby et al., 1998). To ensure the accuracy of using hIg as a marker of MM burden we confirmed that H929/EV and H929/W3A cells produced the same amount of Ig into cultured media (15.5±0.4 and 17.4±0.9 µg/ml per 1×10$^6$ H929/EV and H929/W3a cells, respectively). In vivo circulating level of hIg in sera of H929/W3a-bearing mice was significantly lower than in SCID-hu mice engrafted with EV control H929 cells (p<0.05, FIG. 3C), confirming radiographic evaluation.

Since Wnt signaling directly involved in regulation of osteoblastogenesis and osteoclastogenesis, the numbers of osteoblasts and osteoclasts in bones engrafted with H929/EV and H929/W3A transfected cells were evaluated. These histological analyses revealed significant differences in the cellular composition of the bone in the H929/W3a transfectants in comparison to the control. Bones engrafted with W3A cells had more osteocalcin-expressing osteoblasts and reduced numbers of multinucleated TRAP-expressing osteoclasts on myelomatous bone surface than in H929/EV group (FIGS. 4A, 4B). Taken together, these data indicated that overexpression of Wnt3a has marked inhibitory effect on MM-induced osteolytic bone lesions, an effect that indirectly resulted in slower progression of MM growth.

Example 13

Wnt3a Overexpression Has No Effect On Subcutaneous Growth of H929 MM Cells

To further evaluate whether overexpression of Wnt3a specifically affect MM growth in their natural BM microenvironment, H929/EV and H929/W3a cells were also subcutaneously engrafted in SCID mice. Growth of MM cells which was evaluated by hIg measurements and radiographically revealed no differences in tumor progression over time (FIG. 5A) and final tumor size (FIG. 5B). These data confirmed the in vitro results and suggested that Wnt3a has no direct stimulatory effect on growth of MM cells.

Example 14

Wnt3a Inhibits Primary MM in SCID-Hu Mice

The direct effect of Wnt3a on primary MM bone disease and tumor growth was also examined. SCID-hu mice engrafted with MM cells from 2 patients and upon establishment of MM growth were daily treated with Wnt3a-CM or Cont-CM. It was previously shown that these cells produced approximately 150-200 ng/ml Wnt3a in Wnt3a-CM, based on the ability of Wnt3a-CM and rWnt3a protein to stabilize β-catenin in H929 cells (Qiang et al., 2005). As previously demonstrated growth of primary MM cells was restricted to the human BM microenvironment (Yaccoby et al., 1998; Yaccoby and Epstein, 1999; Yaccoby et al., 2002). BMD of the myelomatous implanted bone in hosts treated with control-CM was reduced from pre-treatment level by 1.9±0.6% while BMD of hosts treated with W3A-CM was increased by 8.0±1.8% from pre-treatment level (p<0.02, FIG. 6A). X-ray radiographs further confirmed preservation of bone loss following W3A-CM treatment and increased osteolytic lesions in bones treated with control-CM (FIG. 6B). Human Ig ELISA revealed that the stimulatory effect of W3A-CM on bone formation was associated inhibition of MM cells growth in these experiments (FIGS. 6C, 6D).

The following references were cited herein:
Abe et al. Blood. 2004; 104: 2484-2491.
Bafico et al. Oncogene. 1998; 16:2819-2825.
Bamias et al. J Clin Oncol. 2005; 23:8580-8587.
Bataille et al. J Clin Invest. 1991; 88:62-66.
Bellido et al. J Biol Chem. 2003; 278:50259-50272.
Bennett et al. Proc Natl Acad Sci USA. 2005; 102:3324-3329.
Berenson et al. N Engl J Med. 1996; 334:488-493.
Binnerts et al. Proc Natl Acad Sci USA. 2007; 104:14700-14705.
Boyden et al. N Engl J Med. 2002; 346:1513-1521.
Coleman et al. J Clin Oncol. 2005; 23:4925-4935.
Colla et al. Blood. 2007; 109:4470-4477.
Cook et al. Embo J. 1996; 15:4526-4536.
Croucher et al. J Bone Miner Res. 2003; 18:482-492.
Day et al. Dev Cell. 2005; 8:739-750.
Derksen et al. Proc Natl Acad Sci USA. 2004; 101:6122-6127.
De Vos et al. Blood. 2001; 98:771-780.
Dosen et al. BMC Immunol. 2006; 7:13.
Edwards et al. Blood. 2007; in Press.
Finch et al. Proc Natl Acad Sci USA. 1997; 94:6770-6775.
Glass et al. Dev Cell. 2005; 8:751-764.
Gong et al. Cell. 2001; 107:513-523.
Grotewold and Ruther. Embo J. 2002; 21:966-975.
Giuliani et al. Blood. 2007; 110:334-338.
Hall et al. Cancer Res. 2005; 65:7554-7560.
Holmen et al. J Biol Chem. 2005; 280:21162-21168.
Hu et al. Development. 2005; 132:49-60.
Johnson and Rajamannan Rev Endocr Metab Disord. 2006; 7:41-49.
Karnoub et al. Nature. 2007; 449:557-563.
Kirstetter et al. Nat Immunol. 2006; 7:1048-1056.
Mikheev et al. Carcinogenesis. 2004; 25:47-59.
Mitsiades et al. Blood. 2003; 101: 2377-2380.
Lacey et al. Cell. 1998; 93: 165-176.
Little et al. Am J Hum Genet. 2002; 70: 11-19.
Nusse R. Cell Res. 2005; 15:28-32.
Oshima et al. Blood. 2005; 106:3160-3165.
Oyajobi et al. Br J Haematol. 2007; 139:434-438.
Pearse et al. Proc Natl Acad Sci USA. 2001; 98:11581-11586.
Polakis P. Genes Dev. 2000; 14:1837-1851.
Qiang et al. Oncogene. 2003; 22:1536-1545.

Qiang et al. Blood. 2005; 106:1786-1793.
Qiang and Rudikoff. Front Biosci. 2004; 9:1000-1010.
Qiang et al. Blood. 2004; 103: 301-308.
Qiang et al. Blood. 2002; 99:4138-4146.
Qiang et al. Exp Hematol. 2000; 28:1147-1157.
Qiang et al. Blood. 2006; 108:977a.
Qiang et al. Blood. 2004; 103:301-308.
Rawadi et al. J Bone Miner Res. 2003; 18:1842-1853.
Reya et al. Immunity. 2000; 13:15-24.
Roodman Blood Cells Mol Dis. 2004; 32:290-292.
Sen M. Rheumatology (Oxford). 2005; 44:708-713.
Sezer et al. Blood. 2003; 101:2094-2098.
Simonet et al. Cell. 1997; 89:309-319.
Spencer et al. J Cell Sci. 2006; 119:1283-1296.
Stewart and Shaughnessy J Cell Biochem. 2006; 98:1-13.
Sukhdeo et al. Proc Natl Acad Sci USA. 2007; 104:7516-7521.
Taube et al. Eur J Haematol. 1992; 49:192-198.
Tian et al. N Engl J Med. 2003; 349:2483-2494.
Vanderkerken et al. Cancer Res. 2003; 63:287-289.
van de Wetering et al. Cell. 2002; 111:241-250.
Veeman et al. Dev Cell. 2003; 5:367-377.
Walker et al. J Clin Oncol. 2007; 25:1121-1128.
Yaccoby et al. Blood. 2006.
Yaccoby et al. Cancer Res. 2004; 64:2016-2023.
Yaccoby et al. Haematologica. 2006; 91:192-199.
Yaccoby et al. Blood. 1998; 92:2908-2913.
Yaccoby and Epstein. Blood. 1999; 94:3576-3582.
Yaccoby et al. Br J Haematol. 2002; 116:278-290.
Yaccoby et al. Blood. 2007; 109:2106-2111.
Yata and Yaccoby. Leukemia. 2004; 18:1891-1897.
Zangari et al. Am J Hematol. 2007; 82:831-833.
Zangari et al. Expert Rev Anticancer Ther. 2007; 7:307-315.
Zangari et al. Br J Haematol. 2005; 131:71-73.
Zhan et al. Blood. 2002; 99:1745-1757.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of repairing or treating lytic bone lesions in an individual with multiple myeloma, comprising:
    expressing Wnt-3a in said individual; and
    blocking the activity of the human homologue of Dickkopf-1 (DKK1), wherein the activity of the human homologue of DKK1 is blocked prior to, concurrent with or subsequent to said expression of the Wnt-3a ligand.

2. The method of claim 1, wherein the expression of Wnt-3a in combination with the blocked activity of the human homologue of DKK1 induces bone anabolic effects in the individual and inhibits tumor growth in the bone.

3. The method of claim 2, wherein the analobic effects comprise inhibition of osteolysis and increasing bone mineral density.

4. The method of claim 1, wherein the activity of the human homologue of DKK1 is blocked by administering anti-DKK1 antibodies.

5. The method of claim 1, wherein the Wnt-3a is expressed by over-expressing a gene encoding Wnt-3a.

6. The method of claim 1, wherein the Wnt-3a is expressed by administering pharmacologically effective amounts of the gene encoding the Wnt-3a directly into the lytic site or by local and/or systemic pulsing for short period of time or by pretreating osteoblast precursor cells with the gene encoding the Wnt-3a for several hours ex-vivo and then injecting the treated precursor cells into the lytic site.

7. The method of claim 1, wherein the gene is delivered by a viral vector or a non-viral gene delivery system.

8. The method of claim 7, wherein the viral vector is an adenoviral vector or a lentiviral vector.

9. The method of claim 7, wherein the non-viral gene delivery system is liposome or a high-pressure gene delivery system.

10. A method of preventing or reducing bone destruction in an individual with multiple myeloma, comprising:
    administering pharmacologically effective amounts of Wnt-3a to said individual, wherein said Wnt-3a increases ratio of ostoeblast to osteoclast and bone mineral density, thereby preventing or reducing bone destruction in the individual;
    administering pharmacologically effective amounts of a compound that blocks the activity of the human homologue of Dickkopf-1 (DKK1), wherein the activity of the human homologue of DKK1 is blocked prior to, concurrent with or subsequent to said expression of the Wnt-3a.

11. The method of claim 10, further comprising:
    controlling tumor growth in the bone of the individual.

12. The method of claim 10, wherein the compound is an anti-DKK1 antibody.

13. The method of claim 10, wherein the Wnt-3a ligand is administered as a gene encoding Wnt-3a.

14. The method of claim 13, wherein the gene encoding the Wnt-3a is directly administered into the lytic site or pulsed systemically and/or locally for short periods of time or indirectly administered by pretreating osteoblast precursor cells with the gene encoding the Wnt-3a for several hours ex-vivo and the injecting the treated precursor cells into the lytic site.

15. The method of claim 13, wherein the gene is delivered by a viral vector or a non-viral gene delivery system.

16. The method of claim 15, wherein the viral vector is an adenoviral vector or lentiviral vector.

17. The method of claim 15, wherein the non-viral gene delivery system is liposome or a high-pressure gene delivery system.

18. A method of inhibiting progression of a tumor in the bone of an individual with multiple myeloma, comprising:
    administering pharmacologically effective amounts of Wnt-3a ligand to said individual, in an amount that prevents bone destruction and inhibits growth of the tumor, thereby inhibiting progression of the tumor in the bone of the individual; and
    administering pharmacologically effective amounts of a compound that blocks the activity of the human homologue of DKK1, wherein the activity of the human homologue of DKK1 is blocked prior to, concurrent with or subsequent to said expression of the Wnt-3a ligand.

19. The method of claim 18, wherein the compound is an anti-DKK1 antibody.

20. The method of claim 18, wherein the Wnt-3a ligand is administered as a gene encoding the Wnt-3a ligand.

21. The method of claim 20, wherein the gene encoding the Wnt-3a ligand is directly administered into a lesion on the bone or pulsed systemically and/or locally for short periods of time or indirectly administered by pretreating osteoblast precursor cells with the gene encoding the Wnt-3a ligand for several hours ex-vivo and then injecting the treated precursor cells into the lytic site.

22. The method of claim 20, wherein the gene is delivered by a viral vector or a non-viral gene delivery system.

23. The method of claim 22, wherein the viral vector is an adenoviral vector or a lentiviral vector.

24. The method of claim 22, wherein the non-viral gene delivery system is liposome or a high-pressure gene delivery system.

* * * * *